United States Patent [19]

Hagiwara et al.

[11] Patent Number: 5,266,070
[45] Date of Patent: Nov. 30, 1993

[54] RELAXATION REFRESHMENT APPARATUS

[75] Inventors: Hiroshi Hagiwara; Kazunori Araki; Akihiro Michimori, all of Kadoma, Japan

[73] Assignee: Matsushita Electric Works, Ltd., Osaka, Japan

[21] Appl. No.: 888,866

[22] Filed: May 27, 1992

[30] Foreign Application Priority Data

| May 28, 1991 | [JP] | Japan | 3-123580 |
| May 28, 1991 | [JP] | Japan | 3-123581 |
| May 28, 1991 | [JP] | Japan | 3-123582 |
| Mar. 19, 1992 | [JP] | Japan | 4-64006 |

[51] Int. Cl.⁵ .......................... A61M 21/00
[52] U.S. Cl. .................................. 600/27
[58] Field of Search .................... 600/26-28

[56] References Cited

U.S. PATENT DOCUMENTS

| 3,014,477 | 12/1961 | Carlin | 600/27 |
| 3,643,941 | 2/1972 | Kashar | 600/28 |
| 3,826,250 | 7/1974 | Adams | 128/33 |
| 4,047,377 | 9/1977 | Banks, Jr. | 58/152 |
| 4,129,123 | 12/1978 | Smidak | 600/28 |
| 4,315,502 | 2/1982 | Gorges | 128/24 |
| 4,553,534 | 11/1985 | Stiegler | 600/28 |
| 4,640,266 | 2/1987 | Levy | 128/25 |
| 4,893,615 | 1/1990 | Khabirova | 128/24 |
| 5,024,650 | 6/1991 | Hagiwara et al. | 128/33 |

FOREIGN PATENT DOCUMENTS

| 2040818 | 2/1972 | Fed. Rep. of Germany . |
| 61-220653 | 9/1986 | Japan . |
| 62-38162 | 2/1987 | Japan . |
| 62-87168 | 4/1987 | Japan . |
| 63-283641 | 11/1988 | Japan . |
| 2201599 | 9/1988 | United Kingdom | 600/26 |

Primary Examiner—Lee S. Cohen
Assistant Examiner—J. P. Lacyk
Attorney, Agent, or Firm—Leydig, Voit & Mayer

[57] ABSTRACT

A relaxation refreshment apparatus includes a relaxation refreshment chair provided for giving to the user a vibratory stimulus variable in accordance with a detected relaxing degree of the user, an optical stimulus with exterior light shielded at the top part of the chair, a pneumatic stimulus operatively connected to an aromatizer nearby, for giving to the user an aromatic stimulus and an acoustic stimulus with a sound output unit, the apparatus being thus capable of intensively providing to the user various stimuli with an arrangement simplified and effectively realizing a compactness with dimensional minimization.

12 Claims, 12 Drawing Sheets

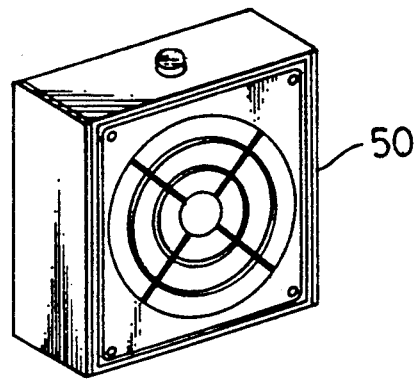
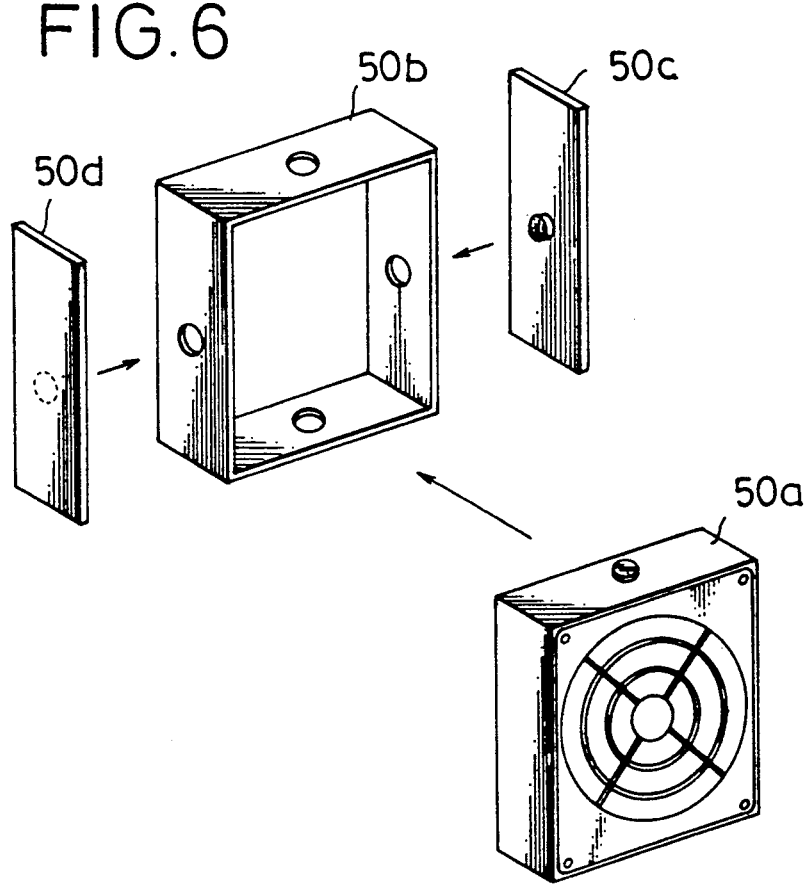

RELAXATION REFRESHMENT APPARATUS

BACKGROUND OF THE INVENTION

This invention relates to relaxation refreshment apparatuses and, more particularly, to an apparatus which provides to the user vibratory, optical, pneumatic and acoustic stimuli in a desired combination to have the user recover from a state of mental fatigue and for realizing mental relaxation and refreshment.

The relaxation refreshment apparatus of the kind referred to finds its utility when used in, for example, highly technological business offices requiring consecutive VDT operation, highly intellectual operation and the like. The invention is useful for quick elimination of mental stress to avoid accumulation thereof.

DESCRIPTION OF RELATED ART

In recent years, growing automation of office facilities has increased VDT (video display terminal) operators attending to document preparation or composition by means of word processors, computer programming and the like. Mental stress caused by the VDT operation for long hours has become an important issue. Not only in the case of VDT operation, but also in the case of other causes such as generally increased commuting distance, mental stresses due to anxiety, displeasure, anger, irritation and so on, the issue of the mental stress has been growing. When mental stress increases, there arises a deterioration in contemplative faculty or attentiveness so that the reaction of an operator will slow so as to render a deterioration of operation efficiency and an increasing frequency of operational mistake or trouble. In eliminating such stress occurring in the operation as in the above, it is encouraged to rest for about ten minutes after every one or two hour of operation, but it has been ascertained that the feeling of fatigue cannot be sufficiently removed by rest alone.

In Japanese Patent Laid-Open Publications Nos. 61-220653 and 62-38162 of Hiroshi Hagiwara et al, there have been disclosed stress dissolving apparatuses in which a chair or bed having portions engageable with the user's back and waist is provided with a plurality of vibrators disposed as mutually separated in height and crosswise directions of the user so that the mental stress can be dissolved by means of an optimum vibration given to the user's body. In another Japanese Patent Laid-Open Publication No. 62-87168 of I. Mihara et al, there has been suggested a brain wave induction system which detects fundamental wave of $\alpha$-wave in human brain waves and generates an output signal of a frequency slightly lower or higher than the detected fundamental wave. The user's sense of sight is stimulated by the output signal in an attempt to reduce the user's mental stress or to provide mental relaxation.

According to these known devices, a result satisfiable to some extent is achievable in respect of stress reduction. In taking a rest during a certain operation and thereafter returning to continue the same operation, however, it is desirable that, after the relaxation achieved by the reduction of stress, the level of the user's consciousness be elevated gradually so as to attain effectively a mental refreshment. In this respect, the known devices still fail to suggest a measure for gradually elevating the level of consciousness after the relaxation achieved. In the prior art the consciousness level is suddenly enhanced after the use of the device or a rather long time is required for reaching an adequate consciousness level for resuming normal operation.

In U.S. Pat. No. 5,024,650 to H. Hagiwara et al, on the other hand, there is disclosed a stress dissolving refreshment system, in which, after an actuation of a relaxed-state induction means for a relaxing period, a refresh stimulus means is actuated to generate a weak stimulus during a disillusion period for gradually elevating the user's consciousness level. A refresh stimulus means is then actuated to generate a strong stimulus during a refreshing period for elevating the user's consciousness level to a level adequate for returning to the normal operation. That system uses properly selective stimuli of various known types in which such optimum vibration of a so-called 1/f fluctuation for the relaxation of the, user, an illumination of 10,000 1× for the purpose of elevating the consciousness level and an air-stream stimulus.

With such known refreshment system, however, required stimulus generating arrangement for complex use of the various stimuli causes a rise in complicacy and dimensional enlargement. That is, the generation of illumination of 10,000 1× requires so many lighting devices, and the air-stream stimulus in combination with other stimuli requires a complicated air supply system.

SUMMARY OF THE INVENTION

A primary object of the present invention is, therefore, to provide an intense relaxation refreshment apparatus provided with respective means for providing various stimuli, while effectively simplifying the arrangement, and capable of allowing the entire apparatus to be compact for promotion of practical use.

According to the present invention, the object is made attainable by means of a relaxation refreshment apparatus in which a relaxed degree of the user is detected by a detecting means, a vibratory stimulus is given to the user by a vibrating means of a relaxation refreshment chair in accordance with the relaxed degree detected, an optical stimulus is given to the head of the user sitting in the chair by an optical stimulus means including lighting equipment and means for scattering incident light from the lighting equipment towards the head of the user while providing a pneumatic stimulus by a pneumatic stimulus means over an area from the head part to neck part, an aromatic stimulus is given to the user with an aroma carried by a blow of air of the pneumatic stimulus, and an acoustic stimulus is provided to the user's auditory sense from an acoustic stimulus means, characterized in that an exterior-light interceptive means or exterior-light shield carrying the optical stimulus means is mounted to a top part of the chair, the pneumatic stimulus means comprises a blower having a blow-off port and disposed adjacent to the top part of the chair, an aromatizer providing the aromatic stimulus is operatively associated with the optical stimulus means and preferably is disposed in linkage to the blower, the acoustic stimulus means comprises a sound output unit which is disposed adjacent to the top part of the chair, and the vibratory, optical, pneumatic, aromatic and acoustic stimuli are provided through a control means in a predetermined time schedule.

All other objects and advantages of the present invention shall become clear from the following description of the invention and with reference to preferred embodiments shown in accompanying drawings.

BRIEF DESCRIPTION OF THE DRAWINGS

FIG. 5 shows in a perspective view a blower employed in the apparatus of FIG. 2;

FIG. 6 is a perspective view as disassembled into parts of the blower of FIG. 5;

Figure 1:
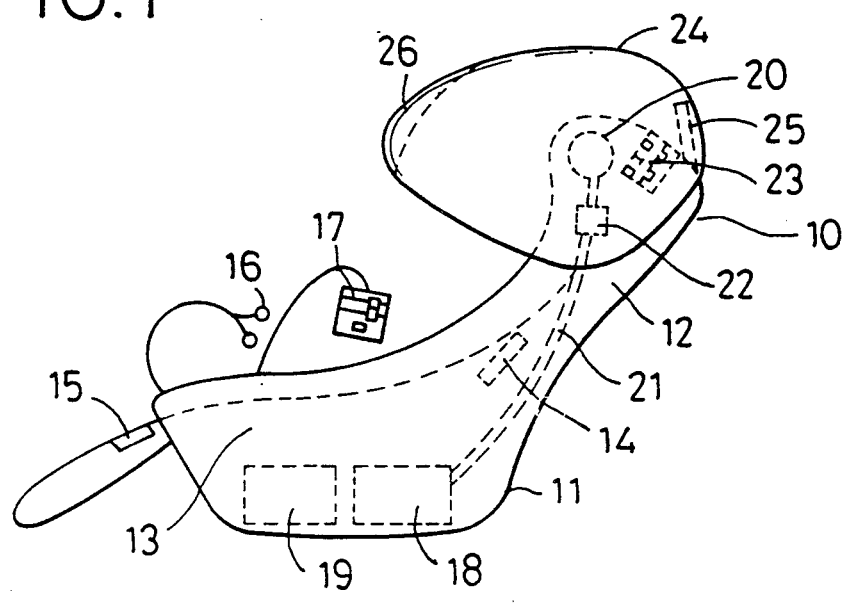
FIG. 1 is a schematic explanatory view of a first embodiment of the relaxation refreshment apparatus according to the present invention.

While the present invention shall now be described with reference to the respective embodiments shown in the drawings, it will be readily appreciated that the intention is not to limit the present invention only to these embodiments shown but rather to include all alterations, modifications and equivalent arrangements possible within the scope of appended claims.

DETAILED DESCRIPTION OF THE PREFERRED EMBODIMENTS

Referring to FIG. 1 showing a first embodiment of the relaxation refreshment apparatus according to the present invention, the apparatus 10 comprises a relaxation refreshment chair 11 which is provided at lower portion of the back 12 and extended end portion of the seat 13 with vibration sources 14 and 15 as vibratory stimulus means, for giving to the user's waist and legs an optimum vibratory stimulus as required. With respect to the seat 13 of the chair 11, a sensor 16 as means for detecting relaxed degree or degree of relaxation of the user as well as an operator 17 for starting the apparatus 10 and placing it in actuating state are provided.

The seat 13 is preferably provided for accommodating therein a blower 18 and a controller 19, so that the blower 18 will communicate through a conduit 21 with a blow-off port 20 provided at top part of the back 12 for providing a blow of air to an area from the head part to neck part of the user sitting and leaning on the chair 11, and thus the blower 18 will act as a pneumatic stimulus means optimumly providing a pneumatic stimulus to the user. An aromatizer 22 acting as an aromatic stimulus means is mounted to a part of the conduit 21, so that an aroma will be carried by the air blow passing through the conduit 21 and blown off from the port 20 for giving to the user an aromatic stimulus together with the foregoing pneumatic stimulus. At the top part of the back 12, such sound output unit 23 as a loudspeaker is provided as an acoustic stimulus means adjacent to the blow-off port 20. Further to the top part of the back 13, a hood 24 is mounted as an exterior light intercepting means in a manner movable between a using position and a non-using position, and lighting equipment 25 and a reflector plate 26 for scattering incident light from the equipment 25 are disposed inside the hood 24 as an optical stimulus means, substantially as opposed to each other.

To the controller 19, an output of the sensor 16 or an operating input from the operator 17 is provided, so that the vibration sources 14 and 15, blower 18, aromatizer 22, sound output unit 23 and lighting equipment 25 will be properly actuated, so as to provide to the user sitting in the chair 11 relaxing and refreshing treatments. Preferably, the vibratory stimulus is varied in a range of 20 to 40 Hz in initial state and in a pattern of 1/f fluctuation and, as the relaxed degree is elevated, the varying range is made narrower to be closer to 30 Hz. From the sound output unit 23 such as a loudspeaker, a music or such masking sound as white noise is reproduced. With the sensor 16, on the other hand, the relaxed degree is measured at regular intervals, for example, at intervals of 3 seconds, the results of the measurement being provided as inputs to the controller 19, the user is then induced to a relaxed state by the vibratory stimulus given for several minutes, this relaxed state is maintained for about seven minutes, thereafter the illuminance of the lighting equipment 25 is elevated and, then, the equipment 25 is made to flash repeatedly for 10 seconds so as to naturally elevate disillusion or awakening level of the user. Thereafter, the illuminance of the lighting equipment 25 should preferably be raised abruptly to be at about 10,000 1× while, at the same time, a cool pneumatic stimulus is provided from the blow-off port 20 for about three minutes with respect to an area from the head part to the neck part of the user, with simultaneous provision of the aromatic stimulus from the aromatizer 22 and the acoustic stimulus from the sound output unit 23, and the awakening level of the user is raised to be good enough for promptly returning to the operation, whereby the mental stress of the user is dissolved preferably within about ten minutes in total.

In the present instance, the relaxation refreshment chair 11 capable of providing the vibratory stimulus is equipped further with the blow-off port 20 of the blower 18 for giving the pneumatic stimulus, aromatizer 22 giving the aromatic stimulus, sound output unit 23 giving the acoustic stimulus and lighting equipment 25 giving the optical stimulus as intensively arranged inside the movable hood 24, so that the entire structure can be simplified to effectively realize the compactness and dimensional minimization.

Figure 2:
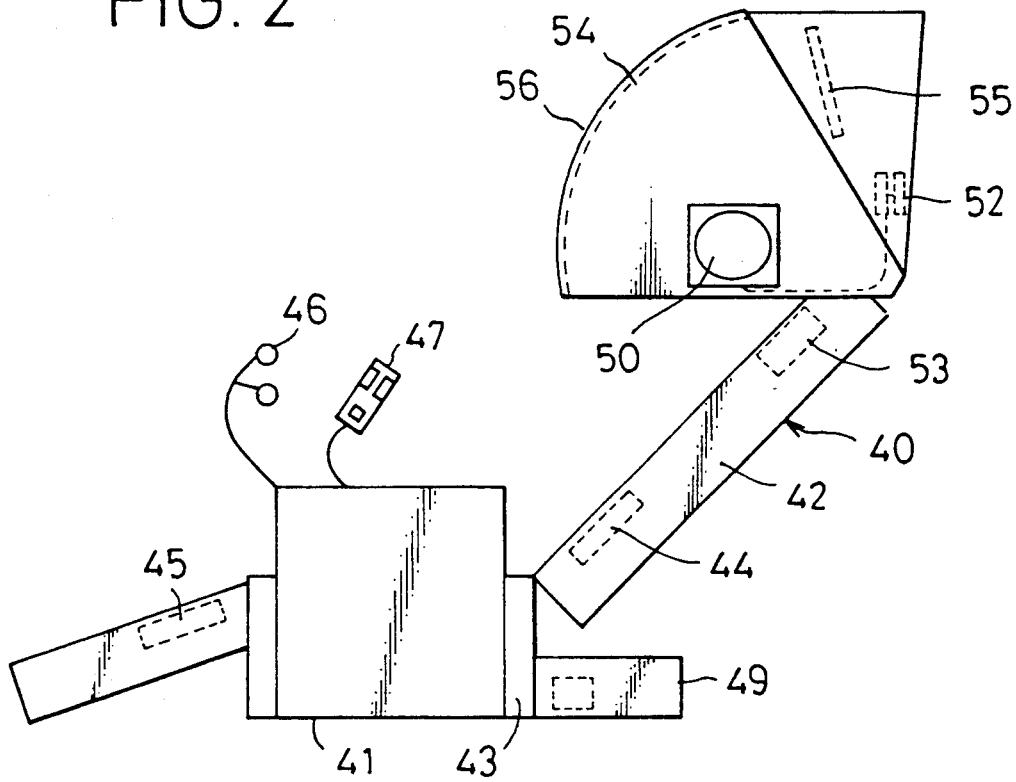
FIG. 2 is a schematic side view of a second embodiment of the apparatus according to the present invention.
Figure 3:
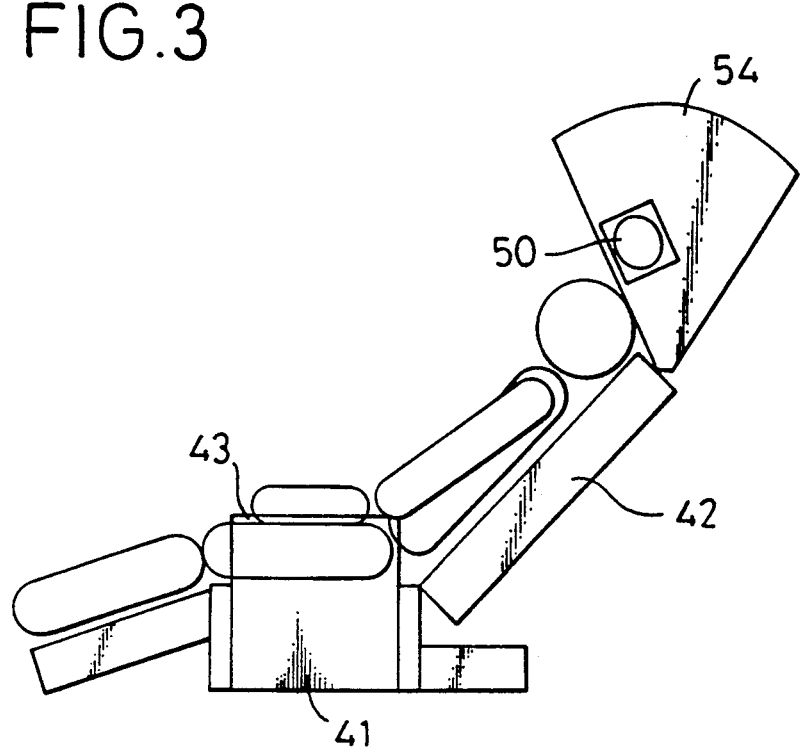
FIG. 3 is an explanatory view for an operating state of the apparatus of FIG. 2.
Figure 4:
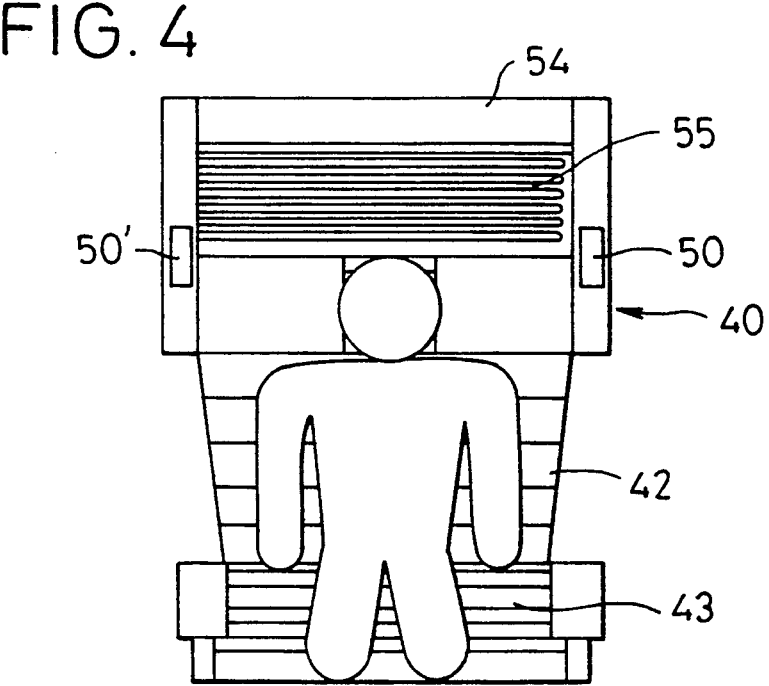
FIG. 4 is a schematic front view of the apparatus of FIG. 2.

Referring next to FIGS. 2 to 4, there is shown schematically a second and more practical embodiment of the relaxation refreshment apparatus according to the present invention, in which substantially the same constituent elements as those in the first embodiment of FIG. 1 are denoted by the same reference numerals as those in FIG. 1 but as added by 30. In this case, the relaxation refreshment chair 41 is provided to be in a reclining type with the back 42 made rotatable when operated by the user, while the chair 41 and hood 54 movably mounted to the chair are provided in the intensive manner similar to the foregoing embodiment with the vibration sources 44 and 45, the blower's blow-off port 50 for the pneumatic stimulus, aromatizer 52 for the aromatic stimulus, sound output unit 53 for the acoustic stimulus and lighting equipment 55 for the optical stimulus. While in the present instance the blow-off port 50 and aromatizer 52 are mounted on the side of the hood 54 and the sound output unit 53 is installed in the back 42 of the chair 41, they may be properly modified in the disposition in accordance with the shape and so on of the chair 41 and hood 54.

Further, the hood 54 is provided to be rotatable between both states shown in FIGS. 2 and 3, that is, between the using state of FIG. 2 and non-using state of FIG. 3, and a pair of the blow-off ports 50 and 50' are provided inside the hood 54 to oppose each other for applying an air flow to the area from the head part to the neck part of the user. As this time, it is preferable to provide the blower and blow-off ports 50 and 50' integrally and for rendering blowing direction to be variable. More specifically, as shown in FIGS. 5 and 6, a main body 50a of the blower is mounted into a square-shaped mounting frame 50b with upward and downward projections of the main body 50a engaged in corresponding holes made in upper and lower sides of the frame 50b, so that the main body 50a will be pivotable about vertical axis of both projections with respect to the mounting frame 50b, whereas the mounting frame 50b itself is mounted between a pair of mounting plates 50c and 50d which are fixed as mutually opposed to proper portion of the hood 54, with sideward projections of these plates engaged in corresponding holes made in both lateral sides of the frame 50b, so that the main body 50a and mounting frame 50b will be pivotable about horizontal axis of both sideward projections with respect to the mounting plates 50c and 50d. Consequently, the main body 50a of the blower is held freely rotatable vertically and horizontally so as to be variable in the direction of air blown out of the blow-off ports 50 and 50'.

Figure 7:
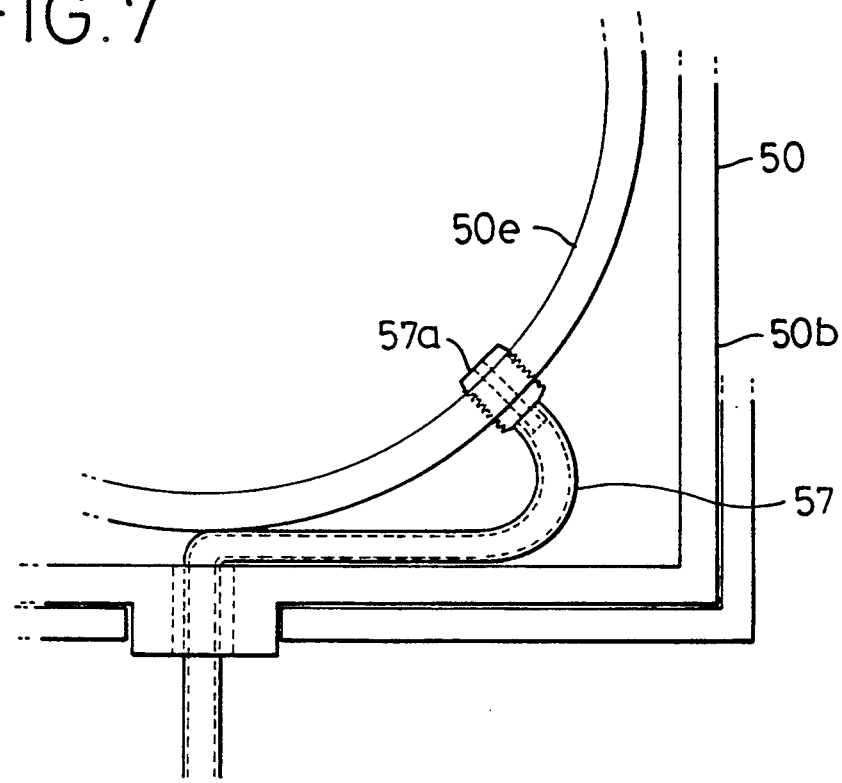
FIGS. 7 and 8 are explanatory views for dispositions of the pneumatic and aromatic stimulus means in the apparatus of FIG. 2.
Figure 8:
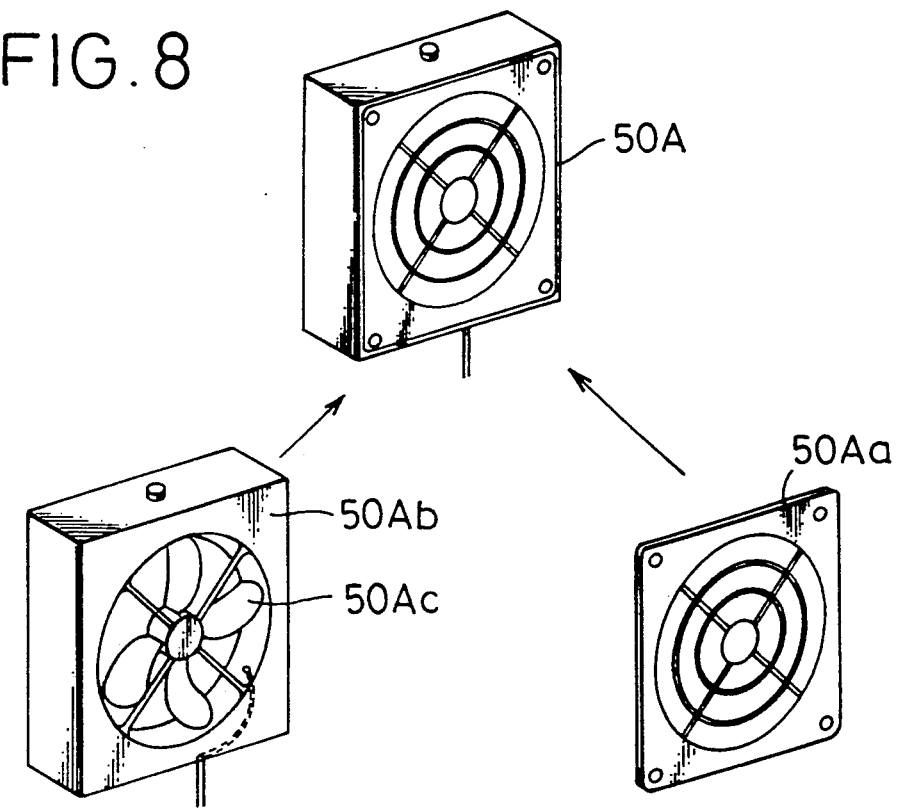

Further, as shown in FIG. 7, at least one of the blow-off ports is provided at its inner frame 50e held inside the mounting frame 50b with an aroma ejection port 57a fixed through the inner frame 50e, while the ejection port 57a itself is coupled to a conduit 57 passing a compressed air flow carrying an aroma sent from the aromatizer 52, whereby the pneumatic stimulus and aromatic stimulus are simultaneously provided from the blow-off ports 50 and 50' to the user. As shown in FIG. 8, on the other hand, a further simplified arrangement may be attained such that a blow-off port 50Aa is assembled with an integral blower body 50Ab incorporating therein a blower fan 50Ac so as to form a pneumatic stimulus means 50A.

Figure 9:
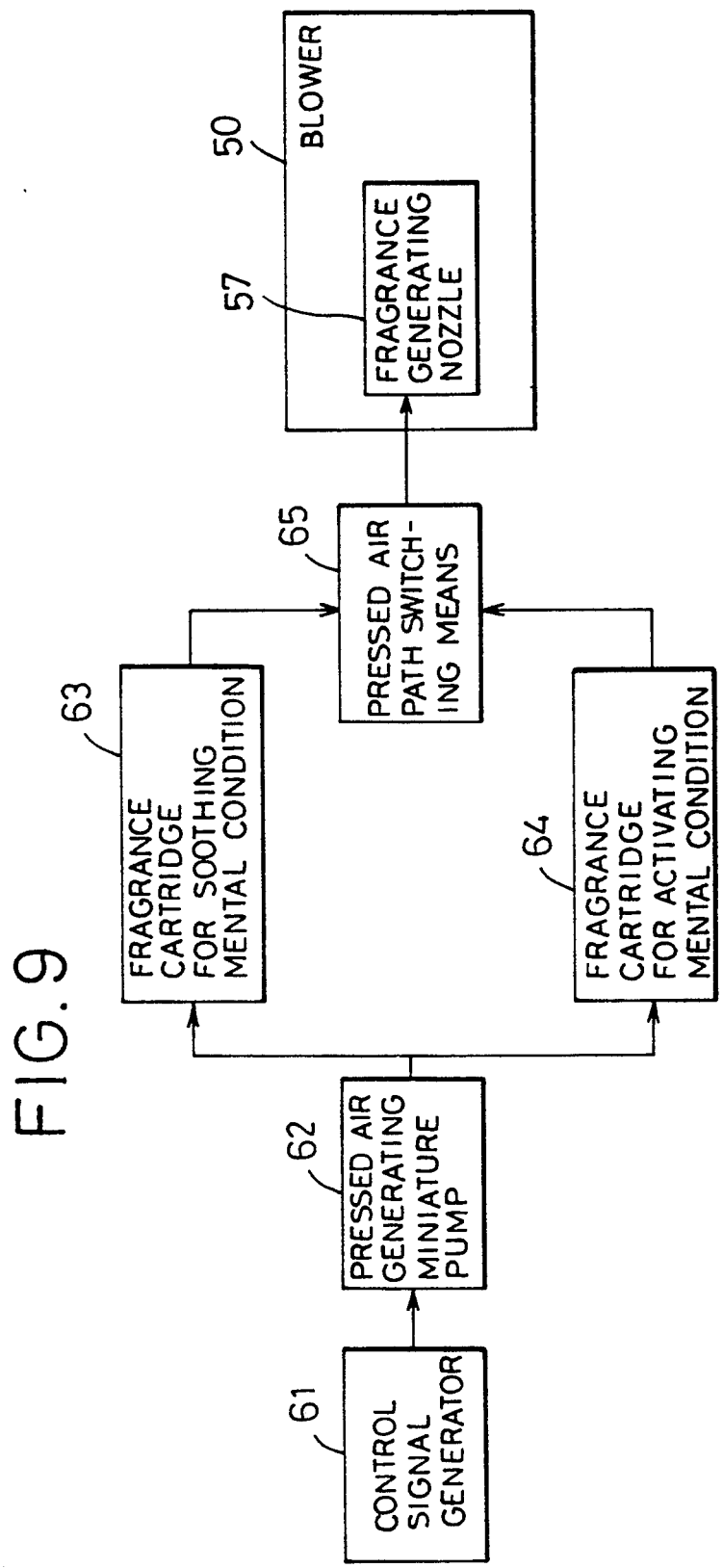
FIG. 9 is a block diagram showing steps of generating the aromatic stimulus in the apparatus of FIG. 2.

For generating the aromatic stimulus, it is preferable to employ such arrangement as shown in FIG. 9. That is, as the user first operates the operator 47 to actuate the controller 49 (FIG. 3) and after a predetermined time lapsed, a control signal generator 61 of the controller 49 sends an actuating signal to a miniature pump 62 for generating a pressurized air, an actuation of which pump a pressurized air is applied to a cartridge 63 of a fragrance effective for soothing the user's mental condition as well as to another cartridge 64 of a fragrance effective for activating the user's mental condition. Both cartridges 63 and 64 are commonly coupled to a pressurized air path switching means 65, so that two flows of the pressurized air which are passed through the fragrance cartridges 63 and 64 to carry respectively the mental condition soothing fragrance and the mental condition activating fragrance are made to reach the path switching means 65. Switching signals are provided to the switching means 65 in accordance with a predetermined relaxation refreshment program so that, in the relaxing period, the switching means 65 opens the air flow path of the mental condition soothing fragrance and, in the refreshing period, the means 65 opens the other path of the mental condition activating fragrance. Thus, the pressurized air passed through the air path switching means 65 carries either one of the two different fragrances through fragrance ejecting nozzle 57 to the blower 50.

Figure 10:
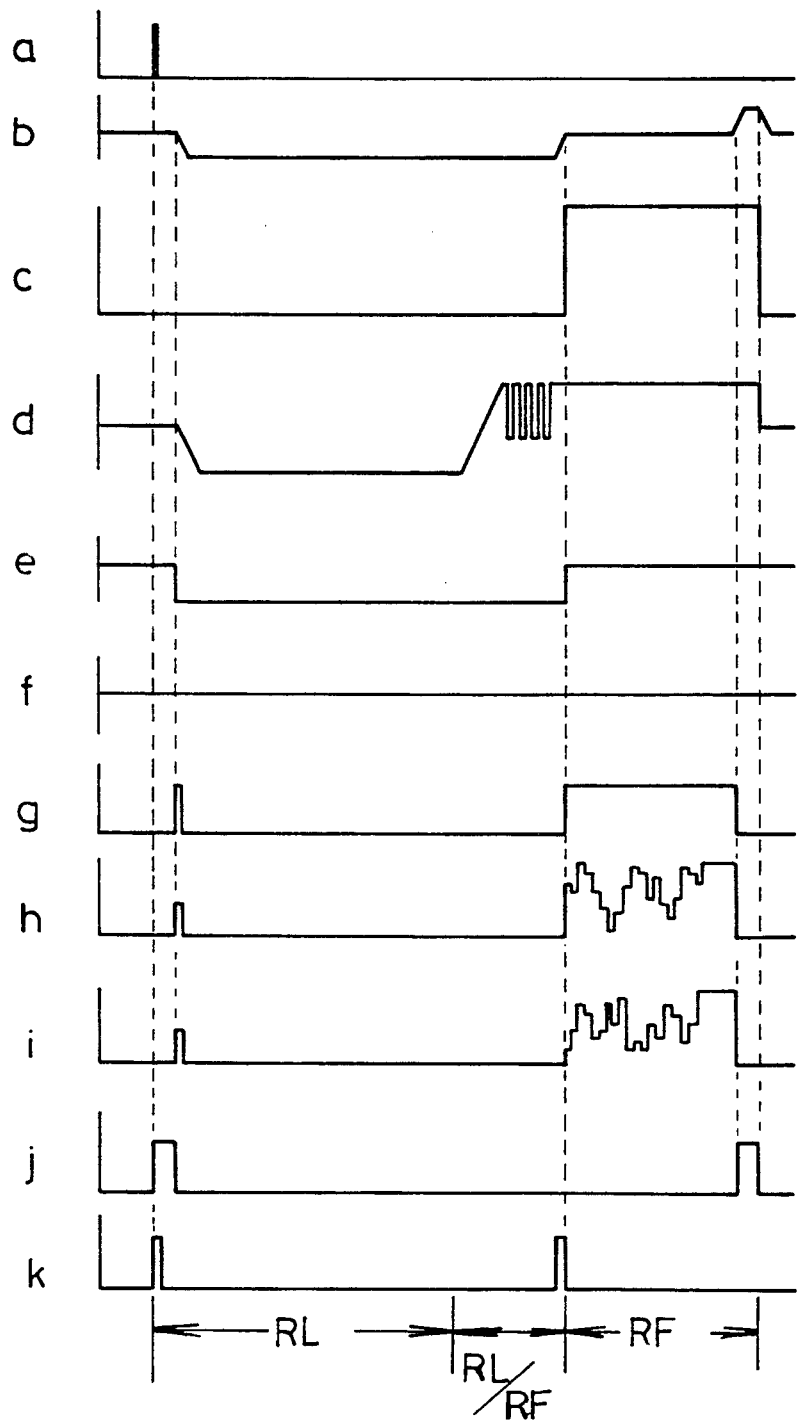
FIG. 10 shows in waveform diagrams (a) to (k) a time chart of respective stimulus generation in the apparatus of FIG. 2.

Referring to FIG. 10, there is shown a time chart in an aspect of the program incorporated in the controller 49. In the drawing, a symbol RL denotes the relaxing period, a symbol RL/RF denotes a transitional period from the relaxing period to the refreshing period, and a symbol RF denotes the refreshing period. In respective waveforms a through k of the drawing, a is a starting signal for driving the controller 49 with the operator 47 actuated by the user. b denotes operating state of the relaxation refreshment chair 41, showing that, in response to the starting signal, the hood 54 is rotated to the using position, the back 42 is gradually inclined to shift to its horizontal position, which position being maintained for the relaxing period RL and transitional period RL/RF, then, as the refreshing period is reached, the back 42 is gradually raised and, as the refreshing period terminates, a state prior to the starting signal is restored. c denotes ON/OFF state of a fluorescent lamp forming part of the lighting equipment 55, showing that the lamp is not lighted ON for the relaxing period RL and transitional period RL/RF, but is lighted ON in the refreshing period RF to emit light of 10,000 1×. d denotes ON/OFF state of a incandescent lamp employed preferably for an indirect illumination of the lighting equipment 55, showing that, prior to the generation of starting signal, the incandescent lamp is kept at lighted ON state of an illuminance of about 500 1×, a reception of the starting signal causes the illuminance inside the hood 54 to be gradually decreased to fully lighted OFF state, and this state is maintained for the relaxing period. As the transition period RL/RF is reached, the illuminance of the incandescent lamp is gradually raised to a fully lighted ON state but is repeatedly lighted OFF and ON in the transitional period, thereafter the fully lighted ON state is maintained during the refreshing period RF and, upon termination of this period, the initial state prior to the starting signal is restored.

Further in FIG. 10, e is of a state of images given by a TV set employed as desired, showing that, when the hood 54 is out of the using position, the TV set is in ON state to provide the image but, when the hood 54 is pivoted to the using position, the TV set is turned OFF to put out the image, and, as the refreshing period is reached, the TV set is turned ON again to provide the image. f represents acoustic state of sound reproduced by such sound output unit 53 as a loudspeaker, showing that the sound is radiated without interruption from the relaxing period RL to the refreshing period RF. g denotes a state in which the pump 62 generating the presurized air blow for carrying the fragrance of the aromatic stimulus, showing that the pump 62 is actuated once at initial stage of the relaxing period RL to have the fragrance for soothing the mental condition provided shortly, and is kept actuated during the refreshing period RF for providing the fragrance for activating the mental condition of the user. In h and i, the operation of the blower 50 or 50A for the pneumatic stimulus is shown, in which the blower is driven once at initial stage of the relaxing period RL for providing shortly the pneumatic stimulus together with the aromatic stimulus of the mental soothing fragrance, and is kept driven in the refreshing period RF for providing continuously the pneumatic stimulus together with the aromatic stimulus of the mental activating fragrance, while the opposed blow-off ports 50 and 50' are preferably provided for being driven mutually independently with differently varied intensity.

Further, j denotes the operating state of the hood 54, showing that, in response to the starting signal for the apparatus 40, the hood 54 is rotated to the using position so that, throughout the respective periods RL, RL/RF and RF the hood can function to restrain any external influence on the user's consciousness while particularly in the refreshing period RF the optical stimulus is effectively given. In the non-using state of the apparatus 40, the hood 54 is rotated to the non-using state at the last stage of the refreshing period, for the sake of a next user. k denotes the operation of the pressurized air path switching means 65, showing that the means is actuated at both of the relaxing and refreshing periods RL and RF for providing the aromatic stimulus with the different fragrances.

Figure 11:
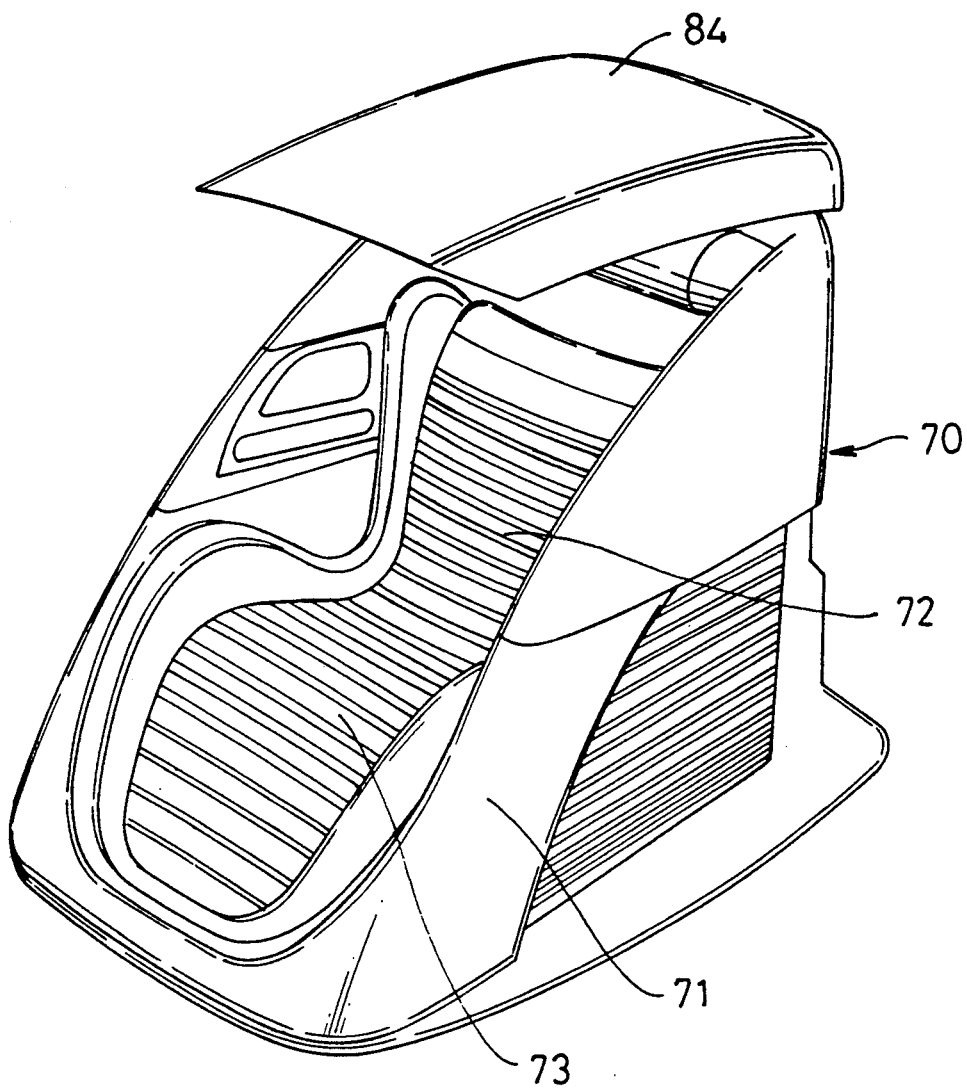
FIG. 11 is a perspective view showing a more practical model of the apparatus of FIG. 2.
Figure 12:
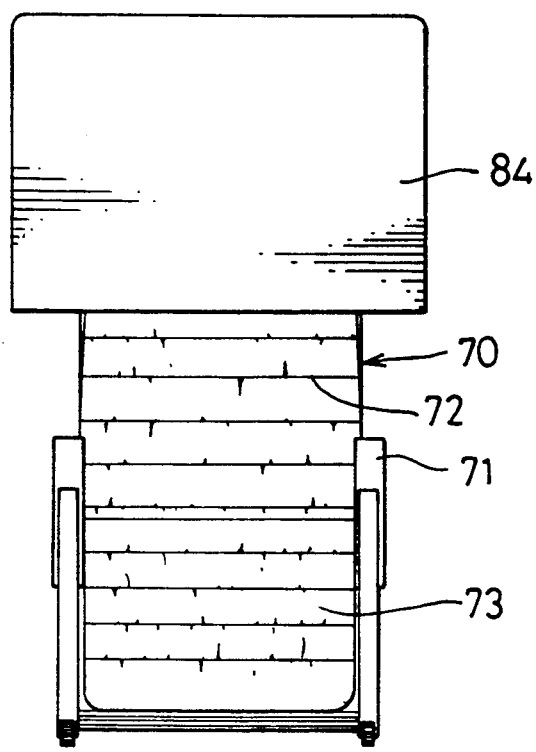
FIG. 12 is a front view of another more practical model of the apparatus of FIG. 2.
Figure 13:
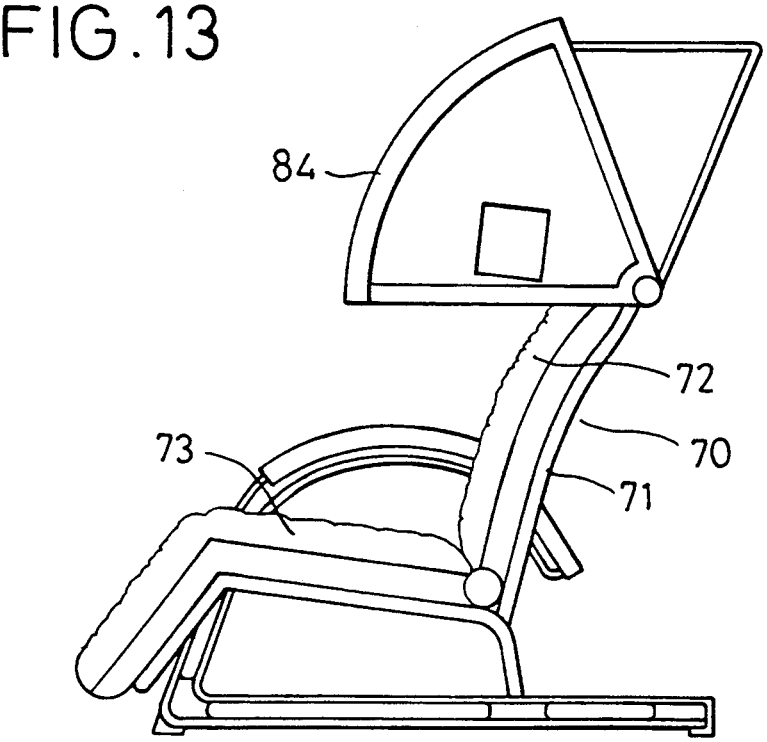
FIG. 13 is a side view of the model shown in FIG. 12.

In FIGS. 11 to 13, there are shown more practical models capable of being put in commerce, in which the same constituent members as those in the embodiment of FIG. 1 are denoted by the same reference numerals as those used in FIG. 1 but with an addition of 60.

Referring to a use aspect of the relaxation refreshment apparatus of the present invention in the practical models, including those which have been already described with reference to the second embodiment of FIG. 2, the illuminance inside the hood by means of a part of the lighting equipment 55 for the optical stimulus in the initial stage is set to be about 500 1×, the user mounts the sensor 46 acting as the relaxed degree detecting means to own finger tips and, after sitting in the reclining relaxation refreshment chair 41, the operator 47 is operated by the user. At this time, an initial value of intensity of the vibratory stimulus is set through the operator 47, the controller 49 is actuated with a start button of the operator 47 depressed, the illuminance by means of the lighting equipment 55 is first gradually reduced and the fully lighted OFF state is attained. The reclining back 42 of the chair 41 is rotated by about 180 degrees, that is, substantially to its horizontal position, and the vibratory stimulus is given to the user's body parts including substantially the waist and legs by means of the vibration sources 44 and 45. In the initial stage, the vibratory frequency is varied in the range of 20 to 40 Hz and in the pattern of 1/f fluctuation, similar to the embodiment of FIG. 1, and this frequency varying range is made narrower as the relaxed degree of the user increases with the time lapsed. The vibratory amplitude, that is, the intensity of the vibratory stimulus is simultaneously weakened.

The relaxed degree of the user is measured by the sensor 46 at regular time intervals of, for example, 3 seconds, and the detection is made on the basis of, for example, the skin electric resistance. At the same time, a music sound or such masking sound as the white noise and the like is produced by the sound output unit 53 as the acoustic stimulus, in order to intercept any external noise.

In this case, the respective stimulus means are controlled by the controller 49 so as to induce the user into a relaxed state within several minutes, and this state is maintained, for example, for about seven minutes. During this relaxing period RL, the user may happen to be put into a slight hypnotic state. As this seven minutes relaxing period RL lapses, the illuminance of the part of the lighting equipment 55 is gradually increased so that the initial illuminance of about 500 1× will be restored after, for example, one minute, the lighting is flashed for ten seconds and the awakening level of the user is gradually elevated. Thereafter, the back 42 of the chair 41 is raised by about 90 degrees, and the illuminance of the lighting equipment 55 is abruptly raised to be about 10,000 1×. Further, the pneumatic stimulus, by means of cool air blown on the head and neck parts of the user for about three minutes through the blow-off ports 50 and 50', together with the aromatic stimulus, by means of the mental activating fragrance carried by the air blown and a user is brought into the refreshed state sufficient to return immediately to the operation. It will be appreciated that the mental stress of the user can be thus eliminated within about ten minutes in total, and the user is put into the state good for prompt returning to the operation.

Figure 14:
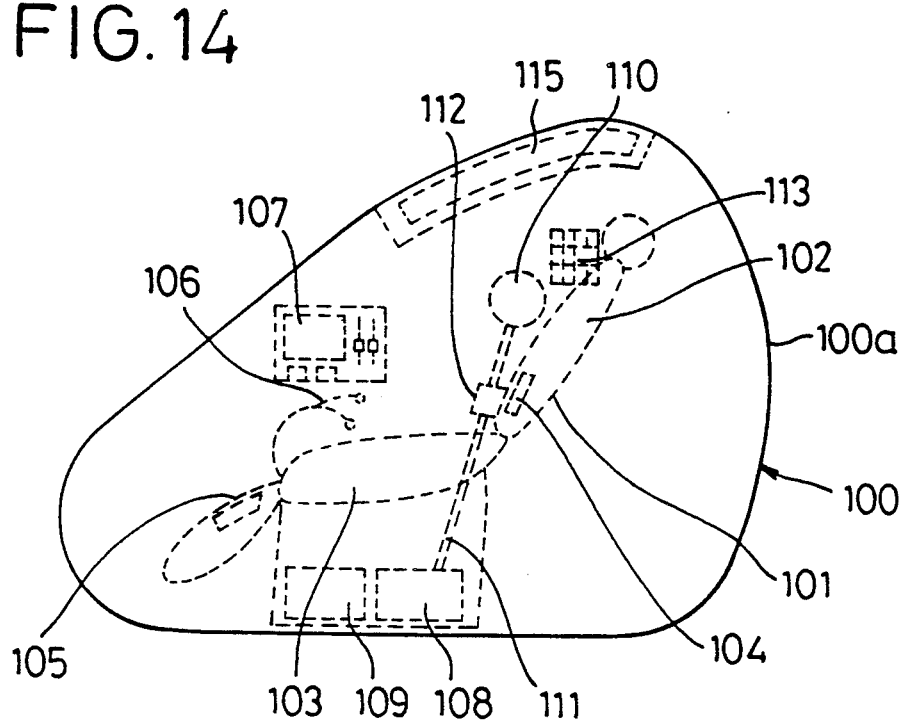
FIGS. 14 and 15 show in schematic side and front views a third embodiment of the relaxation refreshment apparatus according to the present invention.
Figure 15:
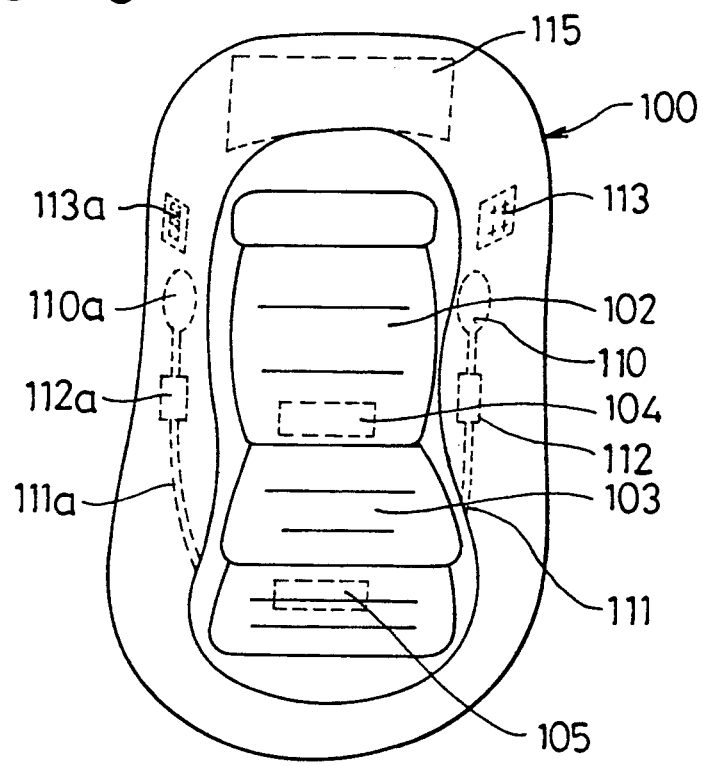

Referring to FIGS. 14 and 15, there is shown a third embodiment of the relaxation refreshment apparatus according to the present invention, in which substantially the same or similar constituent elements as or to those in the embodiment of FIG. 1 are denoted by the same reference numerals as those used in FIG. 1 but with an addition by 90. In the present instance, instead of the hood used in the foregoing embodiments, there is provided a capsule 100a which encloses therein the whole of the reclining relaxation refreshment chair 101, so that the user sitting in this chair can be substantially completely isolated from the exterior. In the present embodiment, the blow-off ports 110 and 110a, conduits 111 and 111a, aromatizers 112 and 112a and sound output units 113 and 113a are disposed in inside walls of the capsule so as to oppose each other on both sides of the chair 101, and the lighting equipment 115 is provided on the inside wall at the top part of the capsule 100a. Other arrangements in this embodiment are the same as those in the foregoing embodiments FIG. 1 and of FIGS. 2 to 4, so that the same functions and effect can be also attained by the present embodiment.

Figure 16:
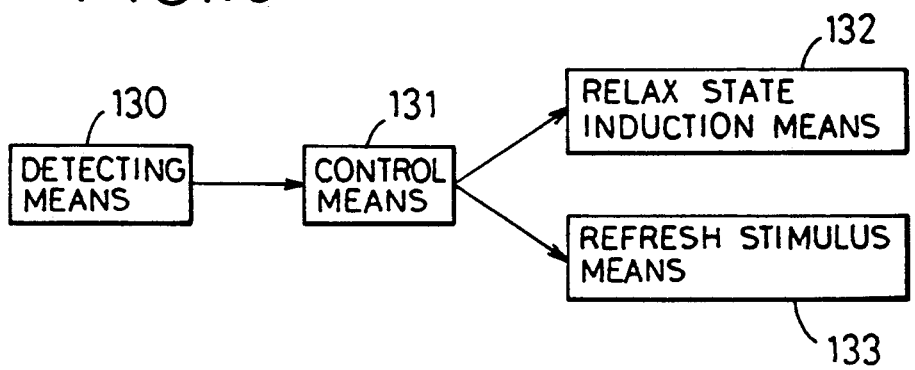
FIG. 16 shows in a block diagram a fourth embodiment of the relaxation refreshment apparatus according to the present invention.
Figure 17:
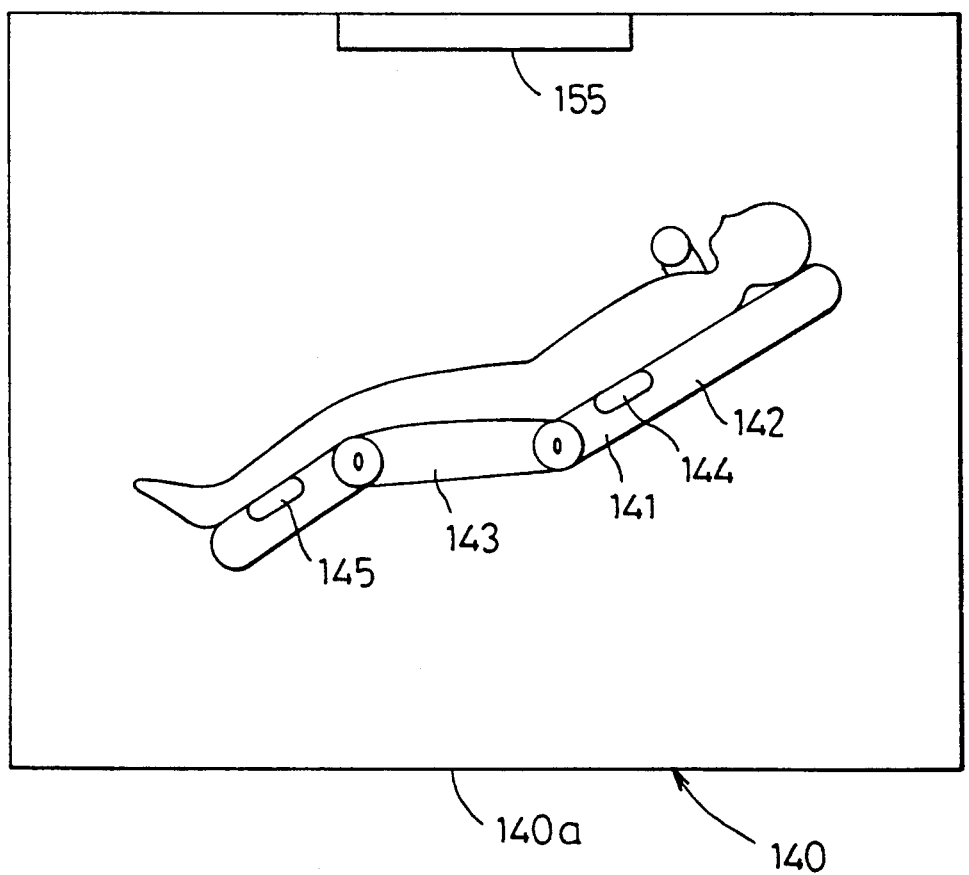
FIG. 17 is an explanatory view for the apparatus of FIG. 16.

According to another feature of the present invention, the apparatus control by the controller is executed on the basis of the electrocardiogram or respiration of the user, instead of the detection of the skin electric resistance. Referring here to FIGS. 16 and 17, the detecting means 130 measures with an electrocardiograph the R—R intervals of the electrocardiogram, detection outputs of the detecting means 130 are provided to a control means 131 for discrimination therein of the relaxed degree and awakening degree of the user. In the present instance, the control means 131 comprises means for storing the R—R intervals of the electrocardiogram in time series, a fast Fourier transformation (FFT) means for frequency-analyzing fluctuation spectrum of the R—R intervals of the electrocardiogram, means for numerically presenting activities of the sympathetic nerves and parasympathetic nerves by measuring the power around 0.1 Hz and the power around 0.3 Hz from results of the frequency-analysis, and means for numerically presenting the degree of physical awakening or mental state on the basis of equilibrium relationship in the activities of the sympathetic and parasympathetic nerves. By this control means, a means of inducing a relaxed state 132 providing mainly the vibratory stimulus or a refreshing stimulus means 133 providing mainly optical, pneumatic and aromatic stimuli for the refreshing by elevating the activity of the parasympathetic nerves higher than that of the sympathetic nerves, is driven. In practice, in the present instance, a relaxation refreshment room 140a is provided for the relaxation refreshment apparatus 140 for isolating the interior thereof from the exterior, the relaxation refreshment chair 141 is disposed in this room 140a, the vibration sources 144 and 145 are disposed respectively at a lower portion of the back 142 and adjacent to the lower end of the seat 143, and the lighting equipment 155 is disposed on an interior surface of the ceiling wall of the room 140. While not shown in FIG. 17, the respective stimulus means are also provided to the relaxation refreshment chair 141 as has been disclosed with reference to FIG. 1 and FIGS. 2 to 4, and substantially the same arrangements as those in the foregoing embodiments, except for the above aspect of the detecting means and related arrangement, attain the same functions and effect.

Figure 18:
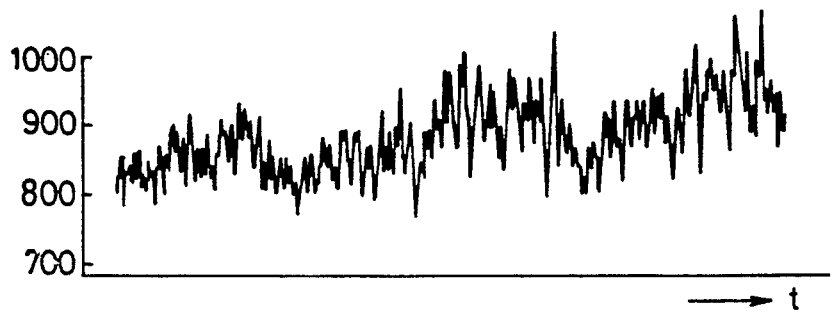
FIG. 18 is a diagram showing time series transition of R—R interval in the electrocardiogram employed in the apparatus of FIG. 16.
Figure 19:
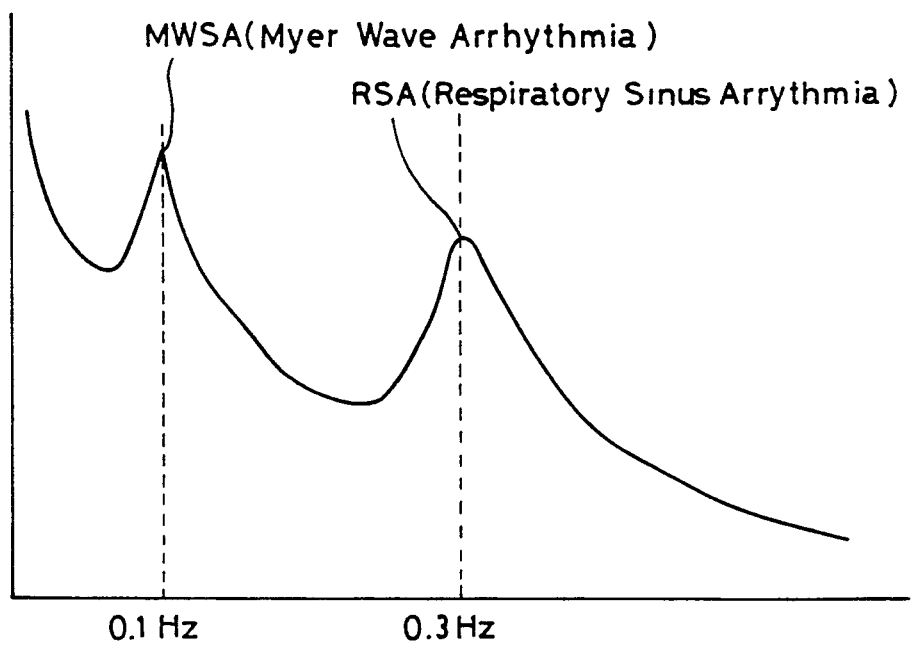
FIG. 19 is a diagram showing fluctuation spectrum of the R—R interval in the electrocardiogram employed in the apparatus of FIG. 16.

In FIG. 18, there is shown a time series of the R—R intervals in the electrocardiogram by the detecting means, while in FIG. 19 there is shown a power spectrum as a result of the frequency analysis of the R—R intervals, in which a respiratory sinus arrhythmia (RSA) around 0.3 Hz reflects the activity of the parasympathetic nerves while a Myer wave (blood pressure) arrhythmia (MWSA) around 0.1 Hz reflects the activities of both of the sympathetic nerves and parasympathetic nerves. Accordingly, it is possible to assume the activities of the sympathetic nerves by dividing MWSA with RSA, or to discriminate the awakening degree by operating the difference in the activity between the sympathetic nerves and the parasympathetic nerves.

Figure 20:
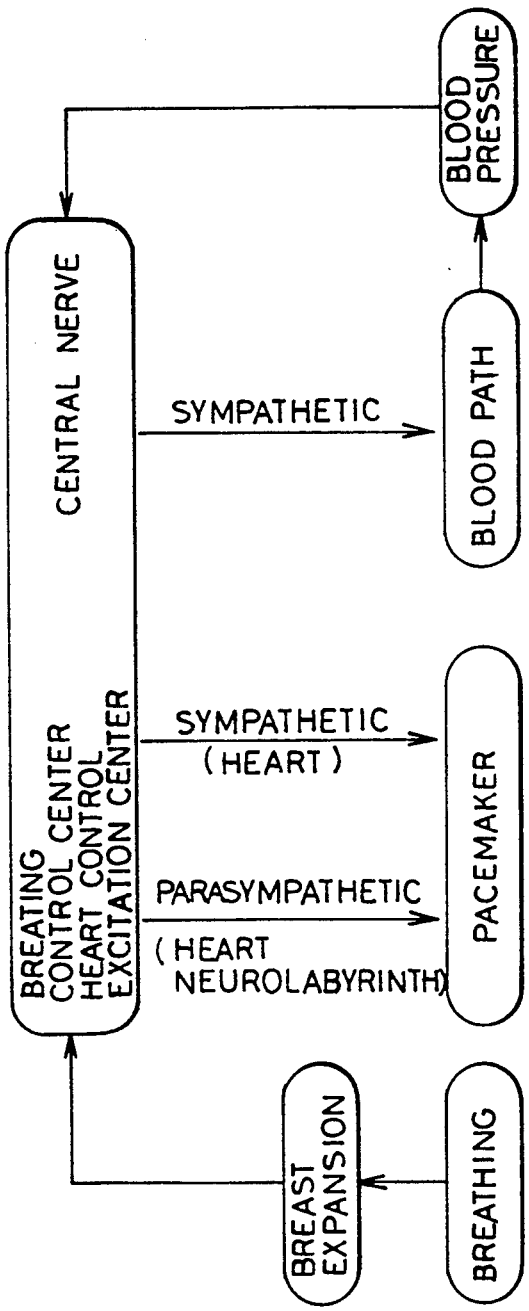
FIG. 20 is an explanatory diagram for the relationship between heart beat fluctuation, respiratory fluctuation and blood pressure fluctuation employed in the apparatus of FIG. 16.

Further, in FIG. 20, there is shown a conceptual explanatory diagram for RSA and MWSA. As will be clear from this diagram, a heart beat pacemaker determining the heart beat cycle is receiving double control of mutually reverse sympathetic nerves (cardiac sympathetic nerves) and parasympathetic nerves (cardiac vagus nerves), and the control is achieved in their equilibrium state. At this time, the sympathetic nerves are effective to attain a promotional action, while the parasympathetic nerves attain a checking or stopping action, with respect to the heart. With respect to bronchial muscles, on the other hand, the sympathetic nerves attain an atony action while the parasympathetic nerves achieve a contractile action. With respect to blood paths, the sympathetic nerves attain the contractile action to raise the blood pressure, while the parasympathetic nerves achieve an expansion action to lower the blood pressure. Accordingly, it will be appreciated that any fluctuation in the heart beat number has a fixed relation to RSA or MWSA, tension degree of the sympathetic and parasympathetic nerves can be discriminated by analyzing the power spectrum of the fluctuation in the R—R intervals of the heartbeat, and the user's awakening degree can be discriminated by determining the activities of the sympathetic and parasympathetic nerves as has been partly described.

We claim:

1. A relaxation refreshment apparatus comprising (a) a detection means for detecting the degree of relaxation a user, (b) a relaxation refreshment chair including (c) a vibratory stimulus means for giving to the user sitting in said chair a vibratory stimulus in accordance with said relaxed degree detected, (d) an external-light shield mounted to a top part of said chair, (e) an optical stimulus means carried by said external-light shield and including lighting equipment and a means to scatter light from said lighting equipment towards the user's head for giving to the user an optical stimulus, (f) a pneumatic stimulus means disposed adjacent to the top part of the chair for giving to an area from the head to the neck of the user a pneumatic stimulus, (g) an aromatic stimulus means including an aromatizer for giving to the user an aromatic stimulus, operatively associated with said pneumatic stimulus means and (h) an acoustic stimulus means including a sound output unit disposed adjacent to the top part of the chair for giving to the user's auditory sense an acoustic stimulus.

2. The apparatus according to claim 1 wherein said to scatter means to scatter light of said optical stimulus means includes means for reflecting light from said lighting equipment within said external-light shield.

3. The apparatus according to claim 1 which further comprises means connected to respective stimulus means for controlling said vibratory stimulus, optical stimulus, pneumatic stimulus, aromatic stimulus and acoustic stimulus according to a predetermined time schedule.

4. The apparatus according to claim 3 wherein said detection means detects at least one of an electrocardiogram and respiration, and said controlling means is actuated by a detection output of the detection means.

5. The apparatus according to claim 4 wherein said controlling means sequentially controls respective said various stimulus means for attaining a relaxation induction and a refreshment stimulus.

6. The apparatus according to claim 1 wherein said external-light shield comprises a movable hood mounted to said top part of said relaxation refreshment chair for rotation between a using position and a non-using position.

7. The apparatus according to claim 6 wherein at least one of the pneumatic stimulus means, aromatic stimulus means, acoustic stimulus means, optical stimulus means and a light reflecting means are included in said hood.

8. The apparatus according to claim 6 wherein said pneumatic stimulus means and said aromatic stimulus means are included in said hood.

9. The apparatus according to claim 1 wherein said pneumatic stimulus means includes a blower with a blow-off port.

10. The apparatus according to claim 9 wherein said aromatizer is in fluid communication with said blower.

11. The apparatus according to claim 9 wherein said blower is formed to be integral with said blow-off port and includes a fan structure.

12. The apparatus according to claim 1 wherein said aromatic stimulus means includes means for aromatically relaxing a user, means for aromatically refreshing a user and means for switching between said aromatic relaxing means and said aromatic refreshing means.

* * * * *

UNITED STATES PATENT AND TRADEMARK OFFICE
CERTIFICATE OF CORRECTION

PATENT NO. : 5,266,070
DATED : November 30, 1993
INVENTOR(S) : Hagiwara et al.

It is certified that error appears in the above-indentified patent and that said Letters Patent is hereby corrected as shown below:

Claim 1, column 10, line 15, after "relaxation" insert --of--.

Claim 2, column 10, lines 34-35, delete "to scatter".

UNITED STATES PATENT AND TRADEMARK OFFICE
CERTIFICATE OF CORRECTION

PATENT NO.   : 5,266,070
DATED        : November 30, 1993
INVENTOR(S)  : HAGIWARA at al.

It is certified that error appears in the above-indentified patent and that said Letters Patent is hereby corrected as shown below:

Column 10, lines 34 and 35, change "said to scatter means" to --said means--.

Signed and Sealed this

Ninth Day of April, 1996

Attest:

BRUCE LEHMAN

Attesting Officer

Commissioner of Patents and Trademarks